United States Patent [19]
Freire et al.

[11] Patent Number: 6,010,612
[45] Date of Patent: Jan. 4, 2000

[54] PRODUCTION OF ISOCYANATE USING CHLORINE RECYCLE

[75] Inventors: Francisco Jose Freire; Bruce Arthur Kaiser, both of Wilmington, Del.; Vinci Martinez Felix, Kennett Square, Pa.; Dennie Turin Mah, Wilmington; James Arthur Trainham, Greenville, both of Del.; Clarence Garlan Law, Jr., West Trenton, N.J.; John Scott Newman, Kensington, Calif.

[73] Assignee: E.I. du Pont de Nemours and Company, Wilmington, Del.

[21] Appl. No.: 08/958,745

[22] Filed: Oct. 1, 1997

Related U.S. Application Data

[63] Continuation of application No. 08/774,284, Dec. 23, 1996, abandoned, and a continuation-in-part of application No. 08/671,867, Jun. 28, 1996, Pat. No. 5,798,036, which is a continuation-in-part of application No. 08/644,551, May 10, 1996, abandoned, which is a continuation-in-part of application No. 08/432,403, May 1, 1995, Pat. No. 5,622,609, which is a continuation-in-part of application No. 08/156,196, Nov. 23, 1993, Pat. No. 5,411,641

[60] Provisional application No. 60/009,340, Dec. 28, 1995.

[51] Int. Cl.$^7$ .............................. C25B 1/00; C25B 3/00
[52] U.S. Cl. ..................... 205/551; 205/436; 205/438; 205/456
[58] Field of Search .................................. 205/436, 438, 205/455, 456, 551

[56] References Cited

U.S. PATENT DOCUMENTS 2,822,373  2/1958  Beck ........................................ 280/848
5,411,641  5/1995  Trainham, III et al. .................. 204/59

FOREIGN PATENT DOCUMENTS 54001281A  1/1979  Japan .

OTHER PUBLICATIONS

Kirk–Othmer, *Encyclopedia of Chemical Technology*, vol. 14, Imaging Technology to Lanthanides (Organic Isocyanates), John Wiley & Sons, Fourth Edition, (1995), pp. 902–934. no month available.

Ullman's *Encyclopedia of Industrial Chemistry*, Fifth Edition, (1989), vol. A19, pp. 412, 413 and 414. no month available.

Minz, F. R. "HCl–Electrolysis—Technology for Recycling Chlorine", Bayer AG, Coference on Electrochemical Processing, Innovation & Progress, Glasgow, Scotland, UK. Apr. 21–23, 1993.

Ullmann's Encyclopedia of Industrial Chemistry, Fifth, Completely Revised Edition, vol. A 14, Immobilized Biocatalysts to Isoprene, pp. 614, 617, 618 and 620, ?/1989.

*Primary Examiner*—Kathryn Gorgos
*Assistant Examiner*—Edna Wong

[57] ABSTRACT

A process and a system produces isocyanate and converts anhydrous hydrogen chloride, which is a by-product of isocyanate production, to chlorine gas in an electrochemical cell. The chlorine is recycled to the isocyanate process. Any unreacted anhydrous hydrogen chloride may be recycled to the electrochemical cell. By recycling the anhydrous hydrogen chloride and the chlorine, the process and system are able to reduce the cost of producing isocyanate. In addition, this process and system process eliminate or at least substantially minimize the problems associated with disposal of anhydrous hydrogen chloride by turning it into a useful starting material in the isocyanate process.

10 Claims, 3 Drawing Sheets

PRODUCTION OF ISOCYANATE USING CHLORINE RECYCLE

This application is a continuation of Application Ser. No. 08/774,284, filed Dec. 23, 1996, now abandoned, which claims the priority benefit of U.S. Provisional Application 60/009,340, filed Dec. 28, 1995, and is also a continuation-in-part of Application Ser. No. 08/671,867, filed Jun. 28, 1996, now U.S. Pat. No. 5,798,036, issued Aug. 25, 1998, which is a continuation-in-part of application Ser. No. 08/644,551, filed May 10, 1996, now abandoned, which is a continuation-in-part of application Ser. No. 08/432,403, filed May 1, 1995, now U.S. Pat. No. 5,622,609, issued Apr. 22, 1997, which was surrendered in favor of reissue application U.S. Application Ser. No. 08/834,014 filed Apr. 11, 1997, which is a continuation-in-part of Application Ser. No. 08/156,196, filed Nov. 22, 1993, now U.S. Pat. No. 5,411,641, issued May 2, 1995, which was surrendered in favor of reissue application U.S. Application Ser. No. 09/093,468 filed Jan. 8, 1998.

BACKGROUND OF THE INVENTION

1. Field of the Invention

The present invention relates to a process and a system for producing isocyanate using chlorine recycle to produce phosgene, which in turn is used in the production of the isocyanate.

2. Description of the Related Art

Isocyanates have become large-volume raw materials for addition polymers, such as polyurethanes, polyureas, and polyisocyanurates. By varying the reactants (isocyanates, polyols, poly-amines, and others) for polymer formation, a myriad of products have been developed ranging from flexible and rigid insulation foams to high modulus exterior parts to high quality coatings and abrasion-resistant elastomers. See Kirk Othmer, *Encyclopedia of Chemical Technology*, Fourth Edition, Volume 14, pp. 902–934 (1995).

A plant, or system, employing a commercial process for producing one widely manufactured type of isocyanate, toluene diisocyanate, is illustrated in the block flow diagram of FIG. 1. The plant is shown generally at 10. Plant 10 includes a dinitro toluene reactor as shown at 12 in FIG. 1. A first inlet feed line 14 as shown in FIG. 1 feeds toluene to the reactor. A second inlet feed line 16 feeds nitric acid to the reactor. The toluene is nitrated using the nitric acid to form dinitro-toluene (DNT). The dinitro-toluene is fed to a reduction reactor 18 through a line 20. In addition, hydrogen gas is fed to reduction reactor 18 through a line 22. The hydrogen gas reduces the nitro groups of the dinitro-toluene to amino groups to produce toluene diamine (TDA). This toluene diamine is sent to a toluene diisocyanate reactor 24 through a line 26 as shown in FIG. 1. Phosgene ($COCl_2$) from a phosgene generator 28 as shown in FIG. 1 is fed to reactor 24 through a line 30. Chlorine is fed to the phosgene generator through a line 32, and carbon monoxide is fed to the phosgene generator through a line 34. The chlorine and the carbon monoxide react to form phosgene, as known in the art. This phosgene reacts with the toluene diamine to form toluene diisocyanate (TDI), which exits through a line 36, and essentially anhydrous hydrogen chloride (AHCl), which exits through a line 38.

The disposal of this anhydrous hydrogen chloride in the isocyanate process presents a problem from an environmental as well as an economic standpoint. This is because discharge of anhydrous hydrogen chloride is environmentally unsound. Moreover, because supply of hydrogen chloride so exceeds demand, it often cannot be sold or used, even after careful purification. Shipment over long distances is not economically feasible.

Therefore, a need exists to develop a simple, inexpensive process for producing an isocyanate in which a by-product of this process, anhydrous hydrogen chloride, can be recycled in the process. Such a process would eliminate or minimize the problems of disposal of anhydrous hydrogen chloride currently associated with the production of isocyanates. In addition, such a process would decrease the cost of production of isocyanates, as it would convert the anhydrous hydrogen chloride by-product into a useful starting material for the isocyanate process.

SUMMARY OF THE INVENTION

The present invention solves the problems of the prior art by providing a process and a system for producing isocyanates which are able to convert anhydrous hydrogen halide into chlorine and hydrogen and which recycles the chlorine to the isocyanate production process. The process and system of the present invention thereby eliminate or minimize the problems associated with disposal of anhydrous hydrogen chloride, and at the same time reduce the cost of producing isocyanates by recycling a useful starting material—i.e., chlorine, to the process.

Moreover, in some isocyanates processes, such as the production of toluene diisocyanates, the hydrogen produced as a result of the electrochemical conversion of anhydrous hydrogen chloride in the system and the process of the present invention may also be recycled to the process in order to make an amine, which is an expensive starting material. In this way, the present invention further reduces the cost of producing toluene diisocyanate.

In addition, the process and system of the present invention are able to directly process anhydrous hydrogen chloride, without the need to convert essentially anhydrous hydrogen chloride to aqueous hydrogen chloride before electrochemical treatment, and the need to remove water from the chlorine gas produced. Therefore, this direct processing of anhydrous hydrogen chloride is less capital intensive and requires lower investment costs than the electrochemical conversions of the prior art.

To achieve the foregoing solutions, and in accordance with the purposes of the invention as embodied and broadly described herein, there is provided a system for producing an isocyanate from chlorine produced by the electrochemical conversion of anhydrous hydrogen chloride, comprising a phosgene generator having a first inlet supply line for supplying chlorine thereto and a second inlet supply line for supplying carbon monoxide thereto, wherein the chlorine and the carbon monoxide react in the phosgene generator to produce phosgene; an isocyanate reactor having a first inlet supply line extending between the phosgene generator and the isocyanate reactor for supplying phosgene thereto and a second inlet supply line for supplying an amine thereto, wherein the phosgene and the amine react in the isocyanate reactor to produce an isocyanate and anhydrous hydrogen chloride; an electrochemical cell, including means for oxidizing the anhydrous hydrogen chloride to produce dry chlorine gas and protons, an anode chamber disposed adjacent the oxidizing means, anode-side inlet means disposed in fluid communication with the anode chamber for introducing the anhydrous hydrogen chloride to the oxidizing means and anode-side outlet means also disposed in fluid communication with the anode chamber for discharging the chlorine gas, cation-transporting means for transporting the protons therethrough, wherein the oxidizing means is disposed in contact with one side of the cation-transporting means, means for reducing the transported protons, wherein the reducing means is disposed in contact with the other side of the cation-transporting means, a cathode chamber disposed adjacent the reducing means, cathode-side inlet means disposed in fluid communication with the cathode chamber for introducing a fluid to the other side of the cation-transporting means and cathode-side outlet means also disposed in fluid communication with the cathode chamber; and a hydrogen chloride supply line extending between the isocyanate reactor and the electrochemical cell for supplying the anhydrous hydrogen chloride produced in the isocyanate reactor to the anode-side inlet means of the electrochemical cell.

Further in accordance with the present invention, there is provided a process for producing an isocyanate from chlorine gas produced by the electrochemical conversion of anhydrous hydrogen chloride, comprising the steps of supplying chlorine from a first inlet supply line to a phosgene generator and supplying carbon monoxide from a second inlet supply line to the phosgene generator, wherein the chlorine and the carbon monoxide react in the phosgene generator to form phosgene; supplying phosgene from the phosgene generator to an isocyanate reactor; supplying an amine to the isocyanate reactor, wherein the amine reacts with the phosgene in the isocyanate reactor to produce an isocyanate and anhydrous hydrogen chloride; supplying the anhydrous hydrogen chloride to an anode-side inlet of an electrochemical cell, wherein the electrochemical cell comprises a cation-transporting membrane, an anode disposed in contact with one side of the membrane and a cathode disposed in contact with the other side of the membrane; applying a voltage to the electrochemical cell so that the anode is at a higher potential than the cathode, and so that the anhydrous hydrogen chloride is transported to the anode and is oxidized at the anode to produce chlorine gas and protons, the chlorine gas is released from an anode-side outlet of the cell, the protons are transported through the membrane of the cell, and the transported protons are reduced at the cathode of the cell; and supplying the chlorine released from the anode-side outlet of the electrochemical cell to the phosgene generator.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

DESCRIPTION OF THE PREFERRED EMBODIMENTS

Reference will now be made in detail to the present preferred embodiments of the invention as illustrated in the accompanying drawings.

In accordance with the present invention, there is provided a system for producing an isocyanate from chlorine produced by the electrochemical conversion of anhydrous hydrogen chloride. Such a system is shown generally at 100 in FIG. 2. This electrochemical conversion directly converts essentially anhydrous hydrogen chloride to dry chlorine gas. The term "direct" means that the electrochemical cell obviates the need to convert the essentially anhydrous hydrogen chloride to aqueous hydrogen chloride before electrochemical treatment. By "anhydrous", or "essentially anhydrous", is meant that the hydrogen chloride is molecular in form, as opposed to aqueous hydrogen chloride, which is ionic in form.

System 100 may be used to make any type of isocyanate, including, but not limited to toluene 2,4-diisocyanate (TDI), toluene 2,6-diisocyanate (TDI), 4,4'-methylene diphenyl diisocyanate (MDI), 2,4'-methylene diphenyl diisocyanate, polymeric methylene diphenyl diisocyanate (PMDI), p-phenylene diisocyanate (PDI) and naphthalene-1,5 diisocyanate (NDI).

Figure 1:
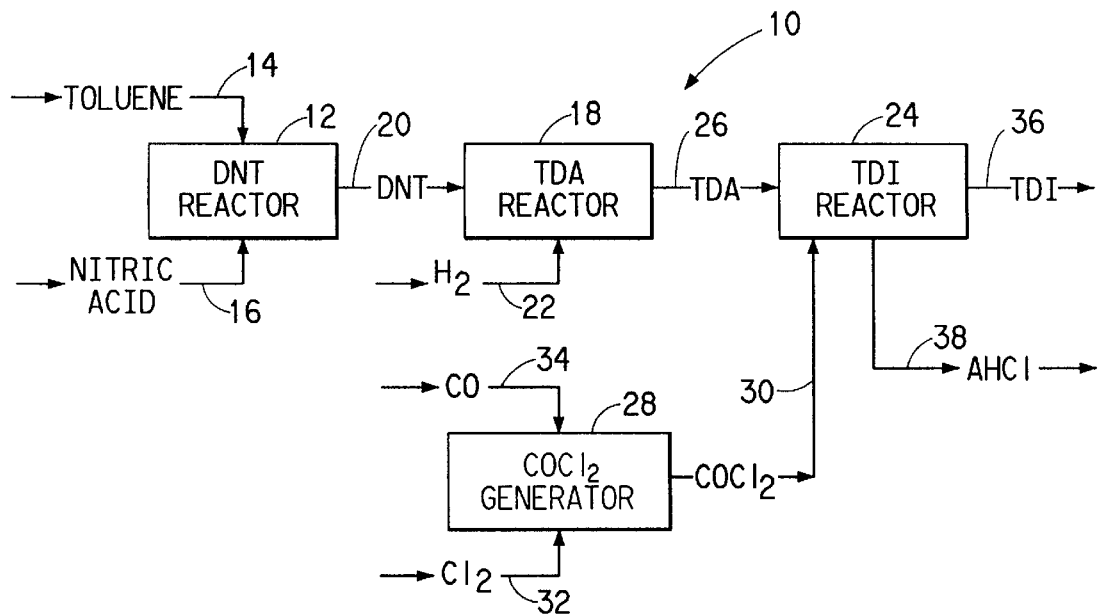
FIG. 1 is a block flow diagram showing a system for producing toluene diisocyanate according to the prior art.
Figure 2:
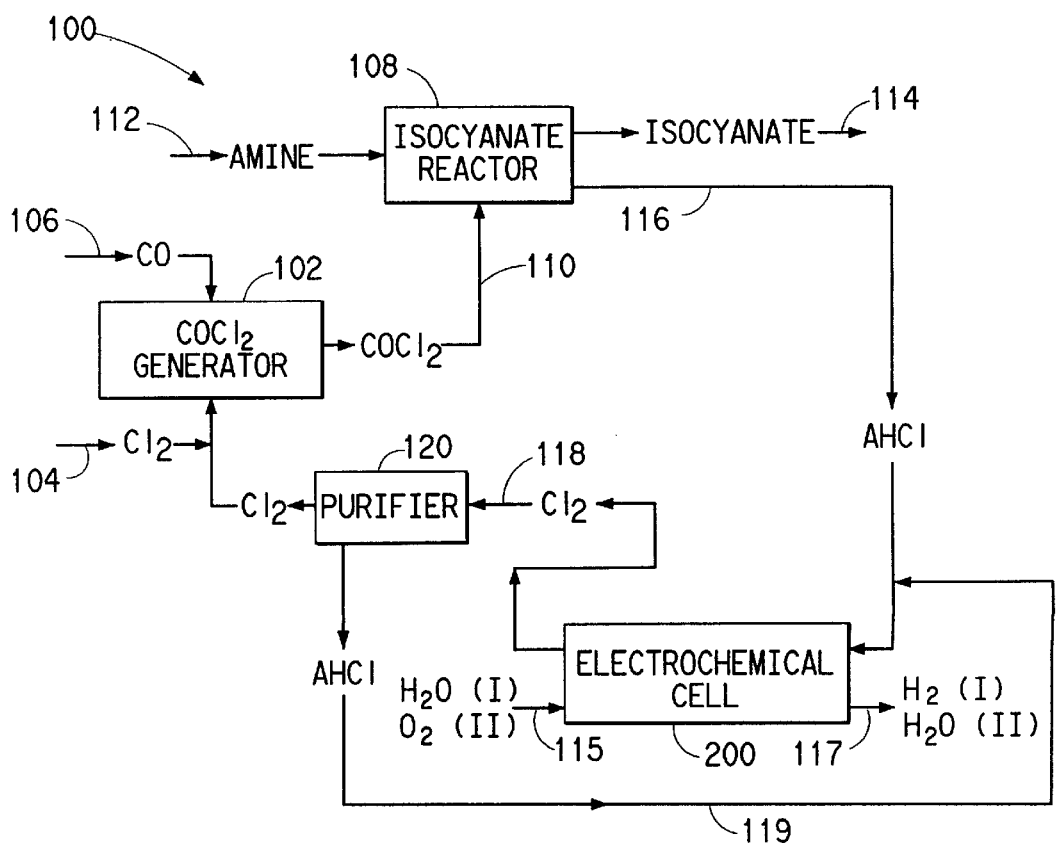
FIG. 2 is a block flow diagram showing a system for producing isocyanate according to the present invention.

System 100 includes a phosgene plant, which includes a phosgene generator shown at 102 in FIG. 2. The phosgene generator has a first inlet supply line 104 for supplying chlorine, which is in the form of liquid dry chlorine, to the phosgene generator and a second inlet supply line 106 for supplying carbon monoxide to the phosgene generator. The carbon monoxide is added in stoichiometric excess of the chlorine to keep the free chlorine content of the phosgene as low as possible. This is because chlorine can lead to the formation of undesirable products during processing of the phosgene. In the phosgene generator, a catalyst may be used to break up the chlorine into chlorine atoms, Cl●. These chlorine atoms react with the carbon monoxide to form phosgene according to the following equation:

$$Cl_2 + CO \rightarrow COCl_2 \tag{1}$$

The system of the present invention also includes an isocyanate reactor. An isocyanate reactor is shown at 108 in FIG. 2. The reactor has a first inlet supply line extending between the phosgene generator and the isocyanate reactor for supplying phosgene to the isocyanate reactor. Such a line is shown in FIG. 2 at 110 extending between the phosgene generator and the isocyanate reactor. The reactor also has a second inlet line for supplying an amine to the isocyanate reactor. Such a line is shown at 112 in FIG. 2. In the isocyanate reactor, the amine reacts with the phosgene to produce isocyanate and essentially anhydrous hydrogen chloride, which is molecular in form. The equation for this reaction is:

$$-(NH2) + COCl_2 \rightarrow -(NCO) + 2AHCl \tag{2}$$

The isocyanate is sent through a line 114 as shown in FIG. 2 for further purification.

Figure 3:
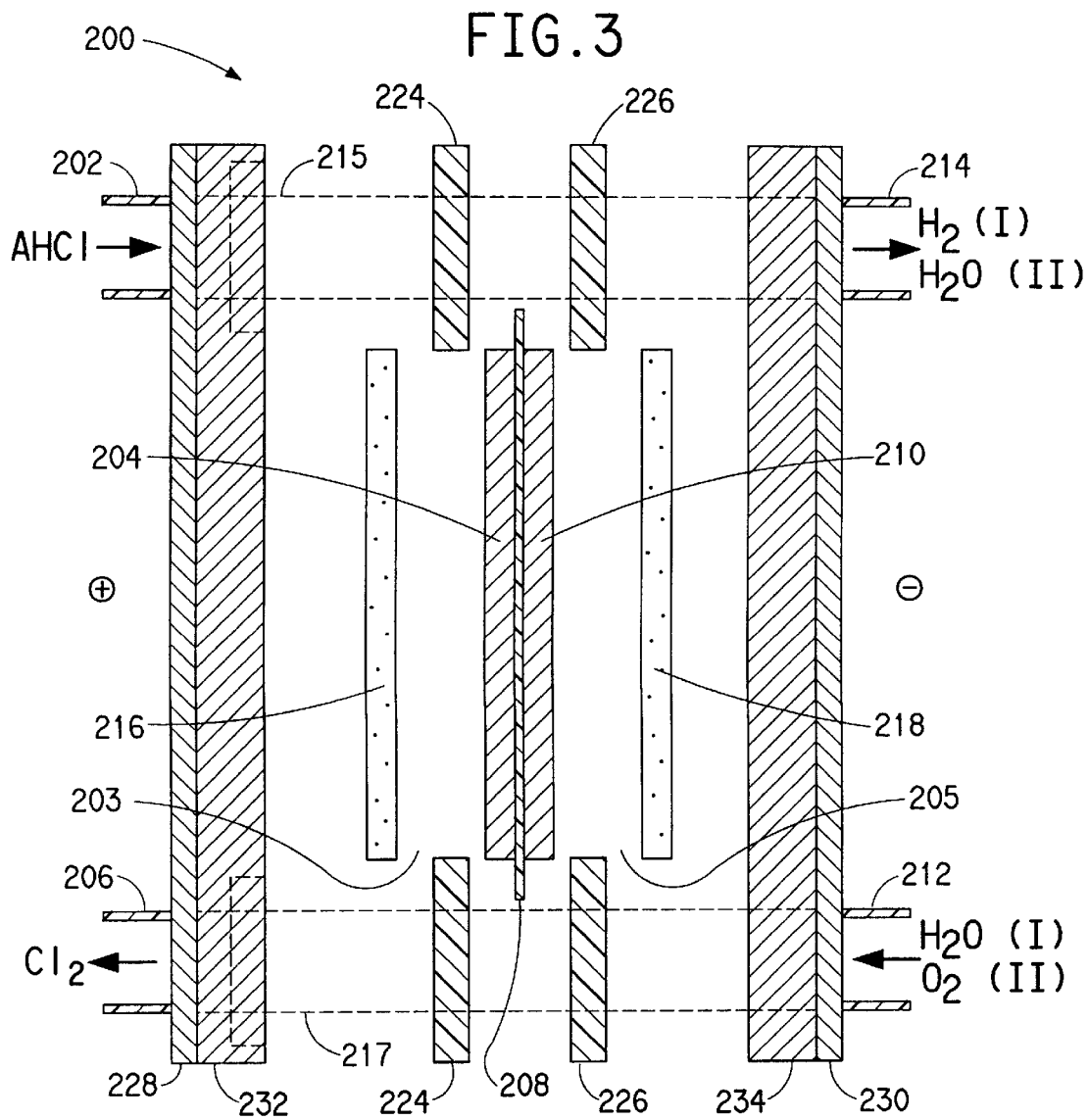
FIG. 3 is a schematic diagram showing the details of an electrochemical cell for producing chlorine gas from anhydrous hydrogen chloride used in the system of FIG. 2.
Figure 4:
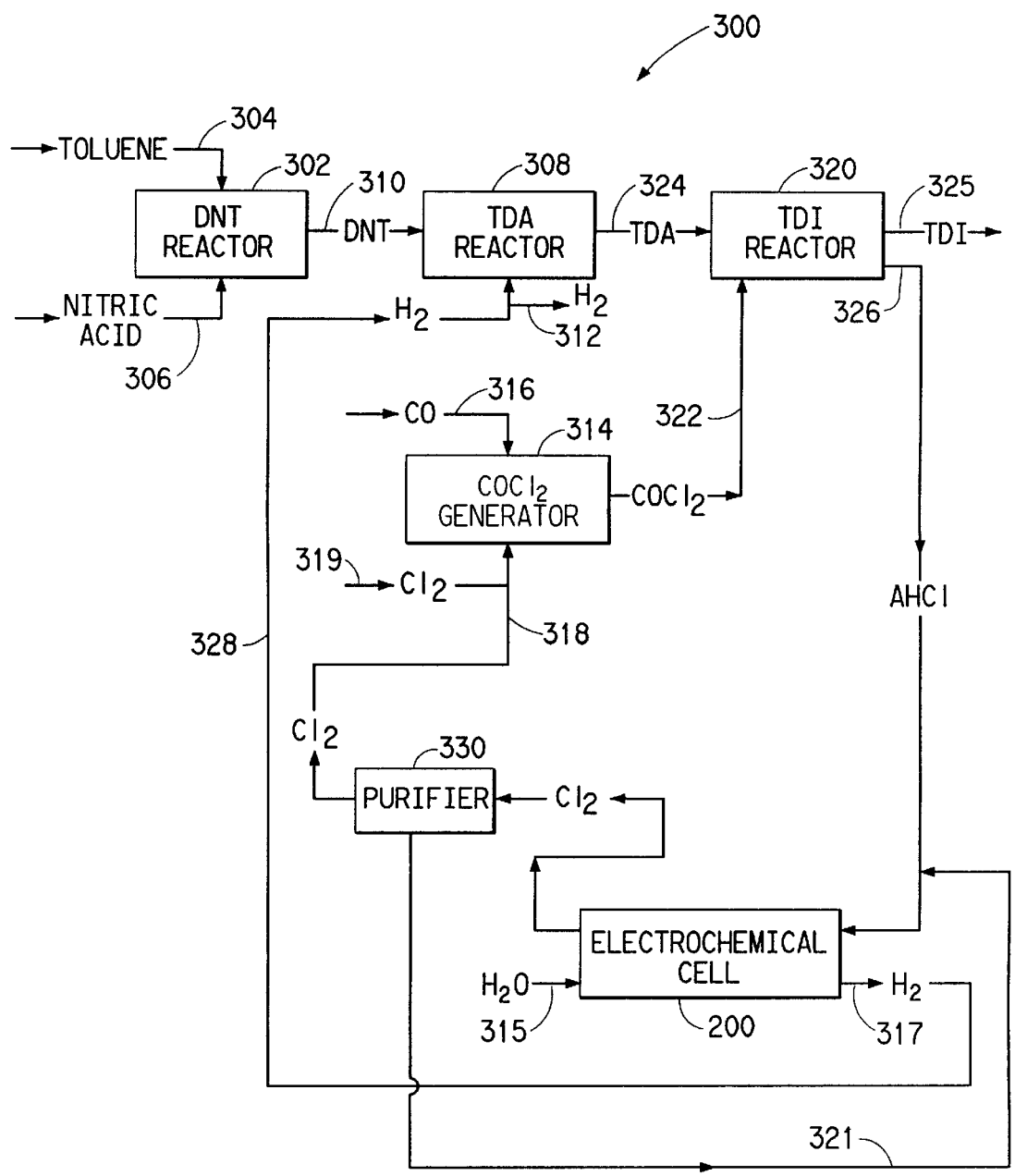
FIG. 4 is a block flow diagram showing a system for producing toluene diisocyanate according to the present invention.

The system of the present invention further includes an electrochemical cell, as shown generally at 200 in FIGS. 2–4. The electrochemical cell of the present invention comprises means for oxidizing the anhydrous hydrogen chloride to produce dry chlorine gas and protons. The oxidizing means comprises an electrode, or more specifically, an anode 204 as shown in FIG. 3. The oxidizing means oxidizes the anhydrous hydrogen chloride to produce chlorine gas, which is essentially dry, and protons. This reaction is given by the equation:

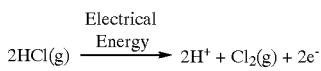

$$2HCl(g) \xrightarrow{\text{Electrical Energy}} 2H^+ + Cl_2(g) + 2e^- \quad (3)$$

The electrochemical cell of the present invention also comprises an anode chamber disposed adjacent the oxidizing means. An anode chamber is shown at 203 in FIG. 3 disposed adjacent, meaning next to or near, the anode. The electrochemical cell of the present invention further includes anode-side inlet means disposed in fluid communication with the anode chamber for introducing the anhydrous hydrogen chloride to the oxidizing means. The anode-side inlet means comprises an anode-side inlet 202 as shown in FIG. 3. The electrochemical cell of the present invention also comprises anode-side outlet means also disposed in fluid communication with the anode chamber for discharging the chlorine gas. The outlet means comprises an anode-side outlet 206 as shown in FIG. 3. A portion of the anhydrous hydrogen chloride may be unreacted, and this unreacted portion leaves the electrochemical cell through the anode-side outlet, along with the essentially dry chlorine gas. Since anhydrous HCl, which is corrosive, is carried through the anode-side inlet, and chlorine gas is carried through the outlet, the inlet and the outlet may be lined with a copolymer of tetrafluoroethylene with perfluoro(alkyl vinyl ether), sold under the trademark TEFLON® PFA (hereinafter referred to as "PFA") by E. I. du Pont de Nemours and Company of Wilmington, Del. (hereinafter referred to as "DuPont").

The system of the present invention further includes a hydrogen chloride supply line extending between the isocyanate reactor and the electrochemical cell for supplying the anhydrous hydrogen chloride produced in the isocyanate reactor to the anode-side inlet means of the electrochemical cell. Such a line is shown at 116 in FIG. 2.

Figure 3A:
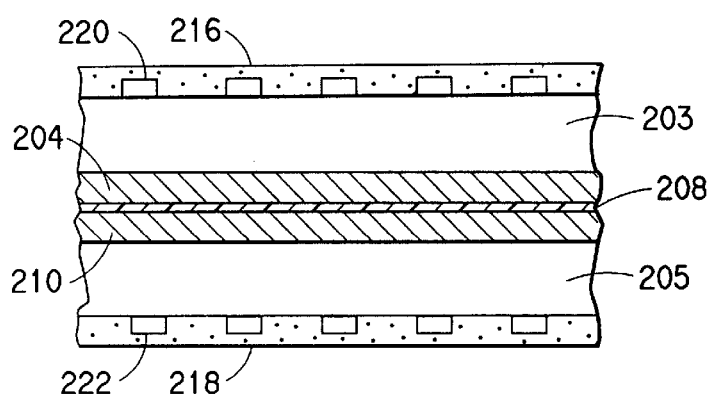
FIG. 3A is a cut-away, top cross-sectional view of the anode and cathode mass flow fields as shown in FIG. 3.

The electrochemical cell of the present invention also comprises cation-transporting means for transporting the protons therethrough, wherein the oxidizing means is disposed in contact with one side of the cation-transporting means. Preferably, the cation-transporting means is a cation-transporting membrane 208, where the anode is disposed in contact with one side of the membrane as shown in FIGS. 3 and 3A. More specifically, membrane 208 may be a proton-conducting membrane. In the present invention, the membrane acts as the electrolyte. The membrane may be a commercial cationic membrane made of a fluoro- or perfluoropolymer, preferably a copolymer of two or more fluoro or perfluoromonomers, at least one of which has pendant sulfonic acid groups. The presence of carboxylic groups is not desirable, because those groups tend to decrease the conductivity of the membrane when they are protonated. Various suitable resin materials are available commercially or can be made according to the patent literature. They include fluorinated polymers with side chains of the type $-CF_2CFRSO_3H$ and $-OCF_2CF_2CF_2SO_3H$, where R is an F, Cl, $CF_2Cl$, or a $C_1$ to $C_{10}$ perfluoroalkyl radical. The membrane resin may be, for example, a copolymer of tetrafluoroethylene with $CF_2=CFOCF_2CF(CF_3)OCF_2CF_2SO_3H$. Sometimes those resins may be in the form that has pendant $-SO_2F$ groups, rather than $-SO_3H$ groups. The sulfonyl fluoride groups can be hydrolyzed with potassium hydroxide to $-SO_3K$ groups, which then are exchanged with an acid to $-SO_3H$ groups. Suitable perfluorinated cationic membranes, which are made of hydrated copolymers of tetrafluoroethylene and perfluoro vinyl ether containing pendant sulfonic acid groups, are offered DuPont under the trademark "NAFION®" (hereinafter referred to as NAFION®). In particular, NAFION® membranes containing pendant sulfonic acid groups include NAFION® 115, NAFION® 117, NAFION® 324 and NAFION® 417. The first and second types of NAFION® are unsupported and have an equivalent weight of 1100 g., equivalent weight being defined as the amount of resin required to neutralize one liter of a 1 M sodium hydroxide solution. NAFION® 324 and NAFION® 417 are both supported on a fluorocarbon fabric, the equivalent weight of NAFION® 417 also being 1100 g. NAFION® 324 has a two-layer structure, a 125 μm-thick membrane having an equivalent weight of 1100 g., and a 25 μm-thick membrane having an equivalent weight of 1500 g. NAFION® 115 in particular may be used with the electrochemical cell of the present invention.

Although the present invention describes the use of a solid polymer electrolyte membrane, it is well within the scope of the invention to use other cation-transporting membranes which are not polymeric. For example, proton-conducting ceramics such as beta-alumina may be used. Beta-alumina is a class of nonstoichiometric crystalline compounds having the general structure $Na_2O_x \cdot Al_2O_3$, in which x ranges from 5 (β"-alumina) to 11 (β-alumina). This material and a number of solid electrolytes which are useful for the invention are described in the *Fuel Cell Handbook,* A. J. Appleby and F. R. Foulkes, Van Nostrand Reinhold, N.Y., 1989, pages 308–312. Additional useful solid state proton conductors, especially the cerates of strontium and barium, such as strontium ytterbiate cerate ($SrCe_{0.95}Yb_{0.05}O_{3-\alpha}$) and barium neodymiate cerate ($BaCe_{0.9}Nd_{0.01}O_{3-\alpha}$) are described in a final report, DOE/MC/24218–2957, Jewulski, Osif and Remick, prepared for the U.S. Department of Energy, Office of Fossil Energy, Morgantown Energy Technology Center by Institute of Gas Technology, Chicago, Ill., December, 1990.

The electrochemical cell of the present invention also comprises means for reducing the transported protons, where the reducing means is disposed in contact with the other side of the cation-transporting means. The reducing means comprises an electrode, or more specifically, a cathode 210, where cathode 210 is disposed in contact with the other side (as opposed to the side which is in contact with the anode) of membrane 208 as illustrated in FIGS. 3 and 3A.

The electrochemical cell of the present invention also includes a cathode chamber disposed adjacent the reducing means. A cathode chamber is shown in FIGS. 3 and 3A disposed adjacent, meaning next to or near, the cathode. The electrochemical cell of the present invention also comprises cathode-side inlet means disposed in fluid communication with the cathode chamber for introducing a fluid to the other side of the cation-transporting means. The cathode-side inlet means comprises a cathode-side inlet 212 as shown in FIG. 3. The cathode-side inlet means is connected to a line, such as line 115 as shown in FIG. 2. The cathode-side inlet introduces a fluid, such as water, to the cathode-side of the membrane in the first embodiment, or an oxygen-containing gas, such as oxygen gas, to the cathode and then to the cathode-side of the membrane in the second embodiment, as will be explained below. The electrochemical cell of the present invention also comprises cathode-side outlet means also disposed in fluid communication with the cathode chamber. The cathode-side outlet means comprises a cathode-side outlet 214 as shown in FIG. 3. The cathode-side outlet is connected to a line, such as line 117 as shown in FIG. 2. Since some chloride ions pass through the membrane and, consequently, HCl is present on the cathode-side of the cell, the cathode inlet and the outlet may also be lined with PFA. A passage 215 as shown in FIG. 3 is formed between the anode-side inlet and the cathode-side outlet, and a similar passage 217 is shown formed between the cathode-side inlet and the anode-side outlet. These passages carry the reactants into and the products out of the cell through the anode and cathode-side inlets, and the anode and cathode-side outlets, as will be further explained below.

The anode and the cathode comprise an electrochemically active material. The electrochemically active material may comprise any type of catalytic or metallic material or metallic oxide, as long as the material can support charge transfer. Preferably, the electrochemically active material may comprise a catalyst material such as platinum, ruthenium, osmium, rhenium, rhodium, iridium, palladium, gold, titanium, tin or zirconium and the oxides, alloys or mixtures thereof. Other catalyst materials suitable for use with the present invention may include, but are not limited to, transition metal macro cycles in monomeric and polymeric forms and transition metal oxides, including perovskites and pyrochores.

The anode and the cathode may be porous, gas-diffusion electrodes. Gas diffusion electrodes provide the advantage of high specific surface area, as known to one skilled in the art. A particular type of gas diffusion electrode, known as an ELAT, may be used as the anode and the cathode. An ELAT comprises a support structure, as well as the electrochemically active material. In one preferred embodiment, an ELAT comprising a support structure of carbon cloth and electrochemically active material comprising ruthenium oxide, commercially available from E-TEK, of Natick, Mass., may be used. Alternatively, an ELAT may be used which comprises a catalyst material mixed with carbon and particles of polytetrafluoroethylene, or PTFE, a fluoropolymer resin which is sold under the trademark "TEFLON®" (hereinafter referred to as "PTFE"), commercially available from DuPont. The catalyst material, carbon particles and PTFE are then sintered on a carbon cloth substrate, which is treated with a NAFION® solution. This ELAT is held mechanically against the membrane of the cell.

Alternative arrangements of the electrochemically active material may be used for the anode and cathode of the present invention. The electrochemically active material may be disposed adjacent, meaning at or under, the surface of the cation-transporting membrane. For instance, the electrochemically active material may be deposited into the membrane, as shown in U.S. Pat. No. 4,959,132 to Fedkiw. A thin film of the electrochemically active material may be applied directly to the membrane. Alternatively, the electrochemically active material may be hot-pressed to the membrane, as shown in A. J. Appleby and E. B. Yeager, Energy, Vol. 11, 137 (1986).

If the electrodes are hot-pressed into the membrane, they have the advantage of having good contact between the catalyst and the membrane. In a hot-pressed electrode, the electrochemically active material may comprise a catalyst material on a support material. The support material may comprise particles of carbon and particles of PTFE. The electrochemically active material may be bonded by virtue of the PTFE to a support structure of carbon cloth or paper or graphite paper and hot-pressed to the cation-transporting membrane. The hydrophobic nature of PTFE does not allow a film of water to form at the anode. A water barrier in the electrode would hamper the diffusion of HCl to the reaction sites.

The loadings of electrochemically active material may vary based on the method of application to the membrane. Hot-pressed, gas-diffusion electrodes typically have loadings of 0.10 to 0.50 mg/cm$^2$. Lower loadings are possible with other available methods of deposition, such as distributing them as thin films from inks onto the membranes, to form a catalyst-coated membrane, as described in Wilson and Gottesfeld, "High Performance Catalyzed Membranes of Ultra-low Pt Loadings for Polymer Electrolyte Fuel Cells", Los Alamos National Laboratory, J. Electrochem. Soc., Vol. 139, No. 2 L28–30, 1992, where the inks contain solubilized NAFION® to enhance the catalyst-ionomer surface contact and to act as a binder to the NAFION® perfluorinated membrane sheet. With such a system, loadings as low as 0.017 mg active material per cm$^2$ have been achieved.

In a preferred embodiment, a thin film of the electrochemically active material is be applied directly to the membrane to form a catalyst-coated membrane (CCM). In this preferred embodiment, the membrane is typically formed from a polymer as described above in its sulfonyl fluoride form, since it is thermoplastic in this form, and conventional techniques for making films from thermoplastic polymer can be used. The sulfonyl fluoride, or SO$_2$F, form means that the side chain, before the membrane is hydrolyzed, has the formula $[-OCF_2CF(CF_3)]n-OCF_2CF_2SO_2F$, n=0–2. Alternatively, the polymer may be in another thermoplastic form such as by having $-SO_2X$ groups where X is a quaternary amine. Solution film casting techniques using suitable solvents for the particular polymer can also be used if desired.

A film of the polymer in sulfonyl fluoride form can be converted to the sulfonate form (sometimes referred to as ionic form) by hydrolysis using methods known in the art. For example, the membrane may be hydrolyzed to convert it to the sodium sulfonate form by immersing it in 25% by weight NaOH for about 16 hours at a temperature of about 90° C. followed by rinsing the film twice in deionized 90° C. water using about 30 to about 60 minutes per rinse. Another possible method employs an aqueous solution of 6–20% of an alkali metal hydroxide and 5–40% polar organic solvent such as dimethyl sulfoxide with a contact time of at least 5 minutes at 50–100° C. followed by rinsing for 10 minutes. After hydrolyzing, the membrane can be converted if desired to another ionic form by contacting the membrane in a bath containing a 1% salt solution containing the desired cation or, to the acid form, by contacting with an acid and rinsing. The membrane used in the membrane-electrode assembly of the present invention is usually in the sulfonic acid form.

The thickness of the membrane can be varied as desired. Typically, the thickness of the membrane is generally less than about 250 $\mu$m, preferably in the range of about 25 $\mu$m to about 150 $\mu$m.

The electrochemically active material is conventionally incorporated in a coating formulation, or "ink", which is applied to the membrane. The electrochemically active material in the form of particles having a particle diameter in the range of 0.1 micron ($\mu$m) to 10 $\mu$m. The coating formulation, and consequently the anode and the cathode after the CCM is formed, also comprises a binder polymer for binding the particles of the electrochemically active material together. The particles of electrochemically active material, when coated with the binder polymer, have a tendency to agglomerate. By grinding the particles to a particularly small size, a better particle distribution may be obtained. Thus, the coating formulation is ground so that the particles have an average diameter of less than 5 $\mu$m, and in many cases, preferably less than 2 $\mu$m. This small particle size is accomplished by ball milling or grinding with an Eiger mini mill, which latter technique can produce particles of 1 μm or less.

The binder polymer is dissolved in a solvent. The binder polymer may be the same polymer as that used for the membrane, as described herein, but it need not be. The binder polymer may be a variety of polymers, such as polytetrafluoroethylene (PTFE). In a preferred embodiment, the binder polymer is a perfluorinated sulfonic acid polymer, and the side chain of the binder polymer, before hydrolyzation of the binder polymer, is represented by the formula [—OCF$_2$CF(CF$_3$)]$_n$—OCF$_2$CF$_2$SO$_2$F (i.e., the SO$_2$F, or sulfonyl fluoride form). The side chain, after hydrolysis, is represented by the formula [—OCF$_2$CF(CF$_3$)]$_n$—OCF$_2$CF$_2$SO$_3$H (i.e., the SO$_3$H, sulfonic acid, or acid form). When the binder polymer is in the sulfonyl fluoride form, the solvent can be a variety of solvents, such as FLUORINERT FC-40, commercially available from 3 M of St. Paul, Minn., which is a mixture of perfluoro(methyl-di-n-butyl)-amine and perfluoro(tri-n-butylamine). In this embodiment, a copolymer polymerized from tetrafluoro-ethylene and a vinyl ether which is represented by the formula CF$_2$=CF—O—CF$_2$CF(CF$_3$)—O—CF$_2$CF$_2$SO$_2$F has been found to be a suitable binder polymer. In addition, ruthenium dioxide has been found to be a suitable catalyst. The sulfonyl fluoride form has been found to be compatible with FC-40 and to give a uniform coating of the ruthenium dioxide catalyst on the membrane.

The viscosity of the ink can be controlled by (i) selecting particle sizes, (ii) controlling the composition of the particles of electrochemically active material and binder, or (iii) adjusting the solvent content (if present). The particles of electrochemically active material are preferably uniformly dispersed in the polymer to assure that a uniform and controlled depth of the catalyst layer is maintained, preferably at a high volume density with the particles of electrochemically active material being in contact with adjacent particles to form a low resistance conductive path through the catalyst layer. The ratio of the particles of electrochemically active material to the binder polymer may be in the range of about 0.5:1 to about 8:1, and in particular in the range of about 1:1 to about 5:1. The catalyst layer formed on the membrane should be porous so that it is readily permeable to the gases/liquids which are consumed and produced in cell. The average pore diameter is preferably in the range of 0.01 to 50 μm, most preferably 0.1 to 30 μm. The porosity is generally in a range of 10 to 99%, preferably 10 to 60%.

The area of the membrane to be coated with the ink may be the entire area or only a select portion of the surface of the membrane. If desired, the coatings are built up to the thickness desired by repetitive application. Areas upon the surface of the membrane which require no particles of electrochemically active material can be masked, or other means can be taken to prevent the deposition of the particles of electrochemically active material upon such areas. The desired loading of particles of electrochemically active material upon the membrane can be predetermined, and the specific amount of particles of electrochemically active material can be deposited upon the surface of the membrane so that no excess electrochemically active material is applied. In a preferred embodiment, the ink is deposited on the surface of the membrane by spraying. However, it should be noted that the catalyst ink may be deposited upon the surface of the membrane by any suitable technique, including spreading it with a knife or blade, brushing, pouring, metering bars and the like. Alternatively, the electrochemically active material may be applied to the membrane by using a screen printing process, as known in the art. An alternative to printing the electrochemically active material directly onto the membrane is the decal process, also known in the art, where the catalyst ink is coated, painted, sprayed or screen printed onto a substrate and the solvent is removed. The resulting decal is then subsequently transferred from the substrate to the membrane surface and bonded, typically by the application of heat and pressure.

After depositing the catalyst layer of electrochemically active material, it is preferable to fix the ink on the surface of the membrane so that a strongly bonded catalyst layer and the cation-transporting membrane can be obtained. The ink may be fixed upon the surface of the membrane by any one or a combination of pressure, heat, adhesive, binder, solvent, electrostatic, and the like. A preferred method for fixing the ink upon the surface of the membrane employs pressure, heat or a combination of pressure and heat. The catalyst layer is preferably pressed onto the surface of the membrane at 100° C. to 300° C., most preferably 150° C. to 280° C., under a pressure of 510 to 51,000 kPa (5 to 500 ATM), most preferably 1,015 to 10,500 kPa (10 to 100 ATM).

If a catalyst-coated membrane as described above is used, the electrochemical cell must include a gas diffusion layer (not shown) disposed in contact with the anode and the cathode, respectively, (or at least in contact with the anode), on the side of the anode or cathode opposite the side which is in contact with the membrane. The gas diffusion layer provides a porous structure that allows the anhydrous hydrogen chloride to diffuse through to the layer of electrochemically active material of the catalyst-coated membrane. In addition, both the anode gas diffusion layer and the cathode gas diffusion layer distribute current over the electrochemically active material, or area, of the catalyst-coated membrane. The diffusion layers are preferably made of graphite paper, and are typically 15–20 mil thick.

When using any type of membrane and electrodes with the present invention, the membrane must be kept hydrated in order to increase the efficiency of proton transport through the membrane. This keeps the conductivity of the membrane high. In the first embodiment, which has a hydrogen-producing cathode, the hydration of the membrane is obtained by keeping liquid water in contact with the cathode-side of the membrane, as will be explained below. For example, when using gas diffusion electrodes, liquid water is delivered to the cathode, and the liquid water passes through the gas-diffusion electrode and contacts the membrane. When using a catalyst-coated membrane, liquid water is delivered to the membrane itself, since the cathode is a thin layer of electrochemically active material applied directly to the membrane.

In particular, in the first embodiment, water is added to the electrochemical cell through cathode-side inlet 212. The protons (H+ in eq. (3) above) which are produced by the oxidation of the anhydrous hydrogen chloride are transported through the membrane and reduced at the cathode to form hydrogen gas, as given by equation (4) below.

(4)

This hydrogen gas is evolved at the interface between the cathode and the membrane. The hydrogen gas, which is shown as H$_2$ (I) for the first embodiment in FIGS. 2 and 3, exits the cell through the cathode-side outlet and through a line 117 as shown in FIG. 2. The hydrogen gas may have some HCl therein due to chloride ion migration. The hydrogen gas may be used for other purposes, such as a fuel, or for producing an amine, as will be explained below.

In the second embodiment, membrane hydration is accomplished by the production of water and by the water introduced in a humidified oxygen-feed or air-feed stream. In particular, in the second embodiment, an oxygen-containing gas, such as oxygen, air or oxygen-enriched air (i.e., greater than 21 mol % oxygen in nitrogen) is introduced through cathode-side inlet 212. Although air is cheaper to use, cell performance is enhanced when enriched air or oxygen is used. This oxygen-containing gas should be humidified to aid in the control of moisture in the membrane, for purposes to be explained below. The oxygen gas ($O_2$) and the transported protons are reduced at the cathode to water, as expressed by the equation:

$$\frac{1}{2} O_2(g) + 2e^- + 2H^+ \rightarrow H_2O(g) \tag{5}$$

The water formed, as illustrated by $H_2O$ (II) in FIGS. 2 and 3, denoting the second embodiment, exits via the cathode-side outlet, along with any unreacted nitrogen and oxygen gas. The water may have some HCl therein due to chloride ion migration, as in the first embodiment.

In the second embodiment, the cathode reaction is the formation of water. This cathode reaction has the advantage of more favorable thermodynamics relative to $H_2$ production at the cathode in the first embodiment. This is because the overall reaction in this embodiment, which is expressed by the following equation:

$$2HCl(g) + \tfrac{1}{2}O_2(g) \xrightarrow{\text{Electrical Energy}} H_2O(g) + 2Cl^- \tag{6}$$

involves a smaller free-energy change than the free-energy change for the overall reaction in the first embodiment, which is expressed by the following equation:

$$2HCl(g) \xrightarrow{\text{Electrical Energy}} H_2(g) + 2Cl^- \tag{7}$$

Thus, the amount of voltage or energy required as input to the cell is reduced in this second embodiment.

Returning again to the description of FIG. 2, the electrochemical cell of the present invention further comprises an anode flow field 216 disposed in contact with the anode and a cathode flow field 218 disposed in contact with the cathode as shown in FIGS. 3 and 3A. The flow fields are electrically conductive, and act as both mass and current flow fields. Preferably, the anode and the cathode flow fields comprise porous graphite paper. Such flow fields are commercially available from Spectracorp, of Lawrence, Mass. However, the flow fields may be made of any material and in any manner known to one skilled in the art. For example, the flow fields may alternatively be made of a porous carbon in the form of a foam, cloth or matte. For the purpose of acting as mass flow fields, the anode mass flow field includes a plurality of anode flow channels 220, and the cathode mass flow field includes a plurality of cathode flow channels 222 as shown in FIG. 3A, which is a cut-away, top cross-sectional view showing only the flow fields of FIG. 3. The anode flow fields and the anode flow channels, get reactants, such as anhydrous HCl in the first and second embodiments, to the anode, and products, such as dry chlorine gas, from the anode. The cathode flow field and the cathode flow channels get catholyte, such as liquid water in the first embodiment, to the membrane, or an oxygen-containing gas to the cathode in the second embodiment, and products, such as hydrogen gas in the first embodiment, or liquid water in the second embodiment, from the cathode.

The electrochemical cell of the present invention may also comprise an anode-side gasket 224 and a cathode-side gasket 226 as shown in FIG. 3. Gaskets 224 and 226 form a seal between the interior and the exterior of the electrochemical cell. Preferably, the anode-side gasket is made of a fluoroelastomer, sold under the trademark VITON® (hereinafter referred to as VITON®) by DuPont Dow Elastomers L.L.C. of Wilmington, Del. The cathode-side gasket may be made of the terpolymer ethylene/propylene/diene (EPDM), sold under the trademark NORDEL® by DuPont, Dow Elastomers L.L.C. or it may be made of VITON®.

The electrochemical cell of the present invention also comprises an anode current bus 228 and a cathode current bus 230 as shown in FIG. 3. The current buses conduct current to and from a voltage source (not shown). Specifically, anode current bus 228 is connected to the positive terminal of a voltage source, and cathode current bus 230 is connected to the negative terminal of the voltage source, so that when voltage is applied to the cell, current flows through all of the cell components to the right of current bus 228 as shown in FIG. 3, including current bus 230, from which it returns to the voltage source. The current buses are made of a conductor material, such as copper.

The electrochemical cell of the present invention may further comprise an anode current distributor 232 as shown in FIG. 3. The anode current distributor collects current from the anode current bus and distributes it to the anode by electronic conduction. The anode current distributor may comprise a fluoropolymer which has been loaded with a conductive material. In one embodiment, the anode current distributor may be made from polyvinylidene fluoride, sold under the trademark KYNAR® (hereinafter referred to as "KYNAR®") by Elf Atochem North America, Inc., fluoropolymers, and graphite.

The electrochemical cell of the present invention may further comprise a cathode current distributor 234 as shown in FIG. 3. The cathode current distributor collects current from the cathode and for distributing current to the cathode bus by electronic conduction. The cathode distributor also provides a barrier between the cathode current bus and the cathode and the hydrogen chloride. This is desirable because there is some migration of hydrogen chloride through the membrane. Like the anode current distributor, the cathode current distributor may comprise a fluoropolymer, such as KYNAR®, which has been loaded with a conductive material, such as graphite.

The electrochemical cell of the present invention also includes an anode-side stainless steel backer plate (not shown), disposed on the outside of the cell next to the anode current distributor, and a cathode-side stainless steel backer plate (also not shown), disposed on the outside of the cell next to the cathode current distributor. These steel backer plates have bolts extending therethrough to hold the components of the electrochemical cell together and add mechanical stability thereto.

When more than one anode-cathode pair is used, such as in manufacturing, a bipolar arrangement, as familiar to one skilled in the art, is preferred. The electrochemical cell of the present invention may be used in a bipolar stack. To create such a bi-polar stack, anode current distributor 232 and every element to the right of the anode current distributor as shown in FIG. 3, up to and including cathode current distributor 234, are repeated along the length of the cell, and current buses are placed on the outside of the stack.

Referring again to the description of FIG. 2, the system of the present invention further comprises a chlorine recycle line extending between the anode-side outlet means of the electrochemical cell and the phosgene generator for supplying the chlorine released from the anode-side outlet means of the electrochemical cell to the phosgene generator. Such a chlorine recycle line is shown at 118 in FIG. 2. The chlorine gas is essentially dry when it is released from the anode side outlet means of the cell. Thus, the system of the present invention may further include a purifier disposed in the recycle line for liquefying and purifying the dry chlorine gas to form liquid dry chlorine. A purifier is shown at 120 in FIG. 2, which is disposed in chlorine recycle line 118.

As noted above, a portion of the anhydrous hydrogen chloride may be unreacted and is released from the anode-side outlet means of the electrochemical cell. The purifier of the present invention also separates the unreacted anhydrous hydrogen chloride in the chlorine recycle line from the chlorine gas. Thus, the system of the present invention may further include a hydrogen chloride recycling line extending between the purifier and the electrochemical cell for recycling the unreacted anhydrous hydrogen chloride to the anode-side inlet of the cell. Such a hydrogen chloride recycle line is shown at 119 in FIG. 2.

Thus, with the system of the present invention as shown in FIG. 2, because the unreacted anhydrous hydrogen chloride may be constantly recycled to the electrochemical cell, much of the chlorine from the anhydrous hydrogen chloride may be recovered. Moreover, this chlorine may be constantly recycled to the phosgene generator. This dual recycle feature of the present invention reduces the cost of producing an isocyanate by ensuring the supply and reducing the cost of chlorine to the isocyanate process. Moreover, this recycle feature eliminates or minimizes the environmental and logistical problems of disposing of anhydrous hydrogen chloride.

As can be seen from FIG. 2, the first inlet supply line to the phosgene generator combines with the chlorine recycle line just before the phosgene generator. This first inlet supply line supplies chlorine to the phosgene generator, in addition to that produced by electrochemical cell 200. This additional, fresh supply of liquid dry chlorine is necessary to make up for losses of chlorine in the system caused by process inefficiencies. However, because of its recycle capability, the system of the present invention is able to recycle much of the chlorine produced by the electrochemical cell, and the amount of additional, or fresh, liquid dry chlorine needed is significantly reduced.

In FIG. 4 there is illustrated a system for making a particular type of isocyanate, in this instance, toluene diisocyanate. This system is shown generally at 300. In the embodiment of FIG. 4, hydrogen gas, as well as chlorine gas, is recycled to the isocyanate process. System 300 includes a dinitrotoluene (DNT) reactor for producing dinitro toluene. Such a reactor is shown at 302 in FIG. 4. Toluene is supplied to dinitrotoluene reactor 302 through a first inlet supply line 304, and nitric acid is supplied to reactor 302 through a second inlet supply line 306. The toluene is nitrated in the dinitrotoluene reactor using the nitric acid to form dinitrotoluene, or DNT, which includes two nitro groups. This reaction is known in the art and is given by the equation:

$$C_6H_5CH_3 + 2HNO_3 \rightarrow CH_3C_6H_3(NO_2)_2 + 2H_2O \qquad (8)$$

The system of the present invention also includes a reduction, or toluene diamine, reactor for producing toluene diamine. Such a reactor is shown at 308 in FIG. 4. The dinitro toluene is supplied to the reduction reactor through a line 310. In addition, hydrogen gas is supplied to toluene diamine reactor 308 through a line 312 as shown in FIG. 4. The hydrogen gas reduces the nitro groups of the dinitrotoluene to an amino group to produce toluene diamine, or TDA, as known in the art. This reaction is given by the equation:

$$CH_3C_6H_3(NO_2)_2 + 4H_2 \rightarrow CH_3C_6H_3(NH_2)_2 + 4 H_2O \qquad (9)$$

In addition, system 300 includes a phosgene generator shown at 314 in FIG. 4. A first inlet supply line 318 supplies chlorine, which is liquid dry chlorine, to the phosgene generator. A second inlet supply line 316 supplies carbon monoxide to the phosgene generator. As explained above, the carbon monoxide is added in stoichiometric excess of the chlorine to keep the free chlorine content of the phosgene as low as possible. Phosgene is produced according to equation (1) above.

The system of the present invention also includes a toluene diisocyanate (TDI) reactor for producing toluene diisocyanate. Such a reactor is shown at 320 in FIG. 4. The reactor has a first inlet supply line 322 as shown in FIG. 4 for supplying phosgene to the isocyanate reactor. Line 322 extends between the phosgene generator and the toluene diisocyanate reactor. The reactor also has a second inlet line 324 as shown in FIG. 4 for supplying toluene diamine to the reactor. In the TDI reactor, the toluene diamine reacts with the phosgene to produce toluene diisocyanate and essentially anhydrous hydrogen chloride, which is molecular in form. The reaction for the formation of the toluene diisocyanate is:

$$CH_3C_6H_3(NH_2)_2 + 2COCl_2 \rightarrow CH_3C_6H_3(NCO)_2 + 4AHCl \qquad (10)$$

The toluene diisocyanate is sent through a line 325 as shown in FIG. 4 for further purification.

The system for producing toluene diisocyanate of the present invention further includes an electrochemical cell as shown generally at 200 in FIGS. 2–4, and as described above, which directly converts anhydrous hydrogen chloride to dry chlorine gas. In addition, the cathode-side inlet of the electrochemical cell is connected to a line, such as line 315 as shown in FIG. 4, and the cathode-side outlet is connected to a line, such as line 317 as shown in FIG. 4.

The system for producing toluene diisocyanate of the present invention further includes a hydrogen chloride supply line extending between the diisocyanate reactor and the electrochemical cell for supplying the anhydrous hydrogen chloride produced in the diisocyanate reactor to the electrochemical cell. Such a line is shown at 326 in FIG. 4.

The system for producing toluene diisocyanate of the present invention further comprises a chlorine recycle line extending between the anode-side outlet means of the electrochemical cell and the phosgene generator for supplying the chlorine gas released from the anode-side outlet means of the electrochemical cell to the phosgene generator. Such a chlorine recycle line is shown at 318 in FIG. 4. The chlorine gas is essentially dry when it is released from the anode side outlet means of the cell. Thus, the system of the present invention may further include a purifier disposed in the recycle line for liquefying and purifying the dry chlorine gas to form liquid dry chlorine. A purifier is shown at 330 in FIG. 4, which is disposed in hydrogen recycle line 318.

As noted above, a portion of the anhydrous hydrogen chloride may be unreacted and is released from the anode-side outlet means of the electrochemical cell. The purifier of the present invention also separates the unreacted anhydrous hydrogen chloride in the chlorine recycle line from the liquid dry chlorine. Thus, the system of the present invention may further include a hydrogen chloride recycling line extending between the purifier and the electrochemical cell for recycling the unreacted anhydrous hydrogen chloride to the anode-side inlet of the cell. Such a hydrogen chloride recycle line is shown at 321 in FIG. 4.

The system of the present invention may further include a hydrogen recycle line extending between the cathode-side outlet means of the electrochemical cell and the toluene diamine reactor. Such a recycle line is shown at 328 in FIG. 4. A purifier (not shown) may be provided in line 328 to dry the hydrogen gas, which is wet when it leaves the electrochemical cell. This recycle line takes the hydrogen gas formed in the first embodiment, when water is added to the cathode-side inlet, from the cathode-side outlet and to the toluene diamine reactor. This hydrogen gas may be used to feed the toluene diamine reaction given in equation (9) above in order to make an amine, which is an expensive starting material. It should be noted that an additional, fresh supply of hydrogen gas may be added to the TDA reactor. This additional, fresh supply of hydrogen gas may be necessary to make up for losses of chlorine in the system caused by process inefficiencies, but the amount of freshly added hydrogen gas is significantly reduced compared to prior art processes.

As can be seen from FIG. 4, as in the system of FIG. 2, the first inlet supply line to the phosgene generator combines with the chlorine recycle line just before the phosgene generator. This first inlet supply line supplies liquid dry chlorine to the phosgene generator, in addition to that produced by electrochemical cell 200 and purified by the purifier. This additional, fresh supply of chlorine is necessary to make up for losses of chlorine in the system caused by process inefficiencies, but again, as with the added hydrogen gas, the amount of freshly added chlorine is significantly reduced compared to prior art processes.

The system of the present invention as shown in FIG. 4 achieves the same benefits associated with the system of FIG. 2—namely, reduced cost of producing isocyanate by the dual recycling feature of recycling both anhydrous hydrogen chloride and chlorine, and elimination or minimization of the problems of disposing of anhydrous hydrogen chloride. In addition, the system of FIG. 4, is able to recycle the hydrogen gas which is released from the cathode-side outlet of the cell. By using the hydrogen gas to feed the toluene diamine reduction reaction as described above, the cost of making toluene diisocyanate may be even further reduced with the present invention.

Further in accordance with the present invention, there is provided a process for producing an isocyanate from chlorine produced by the electrochemical conversion of anhydrous hydrogen chloride to chlorine gas. This process will be described as it relates to the operation of the systems of the present invention as described above with respect to FIGS. 2–4. The process comprises the step of supplying chlorine, which is in the form of liquid dry chlorine, through a first inlet supply line, such as line 104 in FIG. 2 or line 319 in FIG. 4 to a phosgene generator, such as generator 102 as shown in FIG. 2 or generator 314 in FIG. 4. The process also comprises the step of supplying carbon monoxide through a second inlet supply line, such as line 106 in FIG. 2 or line 316 in FIG. 4 to the phosgene generator. The carbon monoxide is added in stoichiometric excess of the chlorine for the reasons noted above. The chlorine and the carbon monoxide react in the phosgene generator to produce phosgene according to equation (1) above. The process also comprises the step of supplying the phosgene from the phosgene generator to an isocyanate reactor, such as isocyanate reactor 108 in FIG. 2 or toluene diisocyanate reactor 320 in FIG. 4. The process also comprises the step of supplying an amine to the isocyanate reactor. The amine reacts with the phosgene in the isocyanate reactor to produce an isocyanate and anhydrous hydrogen chloride, according to equation (2) or equation (10) above.

The anhydrous hydrogen chloride is supplied to an anode-side inlet of an electrochemical cell, such as cell 200 as shown in FIGS. 2–4. A voltage is applied to the electrochemical cell so that the anode is at a higher potential than the cathode and so that the molecular anhydrous hydrogen chloride is transported through flow channels, such as channels 220 in anode mass flow field 216 and to the surface of the anode and is oxidized at the anode to produce chlorine gas and protons ($H^+$). The chlorine gas is released from an anode-side outlet of the cell, such as anode-side outlet 206 as shown in FIG. 3.

The protons produced in the electrochemical cell are transported through the membrane, which acts as an electrolyte. The transported protons are reduced at the cathode. A cathode current distributor 234 collects current from cathode 210 and distributes it to cathode bus 230. In the first embodiment, in order to maintain hydration of the membrane, water is delivered to the membrane at the cathode-side through a cathode-side inlet, such as inlet 212 as shown in FIG. 3, and through the channels in the cathode mass flow field, such as channels 222 in cathode mass flow field 218 as shown in FIG. 3A to hydrate the membrane and thereby increase the efficiency of proton transport through the membrane. The hydrogen gas which is evolved at the interface between the cathode and the membrane as described above exits via a cathode-side outlet, such as outlet 214 as shown in FIG. 3. In the second embodiment, in order to maintain hydration of the membrane, an oxygen-containing gas, such as oxygen ($O_2(g)$), which is preferably humidified, is introduced through a cathode-side inlet, such as inlet 212, and through the channels formed in the cathode mass flow field, such as channels 222 in flow field 218 as shown in FIG. 3A. Oxygen and the transported protons are reduced at the cathode to form water, as explained above. The water exits via a cathode-side outlet, such as outlet 214 as shown in FIG. 3.

The process of the present invention further comprises the step of supplying the chlorine gas released from the anode-side outlet means of the cell to the phosgene generator. The chlorine gas is supplied through a chlorine recycle line, such as line 118 as shown in FIG. 2 or line 318 as shown in FIG. 4. The chlorine gas released from the anode-side outlet means of the cell is essentially dry. The process of the present invention further includes the step of liquefying the dry chlorine gas in a purifier, such as unit 120 in FIG. 2 or purifier 330 in FIG. 4 to form liquid dry chlorine. The process of the present invention further includes the step of supplying an additional supply of liquid dry chlorine to the phosgene generator through the first inlet supply line, such as line 104 in FIG. 2 or 319 in FIG. 4.

A portion of the anhydrous hydrogen chloride may be unreacted in the electrochemical cell. This unreacted portion is released from the anode-side outlet means of the electrochemical cell through an anode-side outlet, such as outlet 206, along with the essentially dry chlorine gas. The process of the present invention includes the step of separating the unreacted anhydrous hydrogen chloride from the liquid dry chlorine in a purifier, such as purifier 120 in FIG. 2 or 330 in FIG. 4. The present invention thus may further include the step of recycling the unreacted anhydrous hydrogen chloride to the anode-side inlet of the electrochemical cell through a recycle line, such as line 119 as shown in FIG. 2 or line 321 in FIG. 4.

In particular, when toluene diisocyanate is produced, the process of the present invention further includes the step of nitrating toluene in a dinitro toluene reactor, such as reactor 302 as shown in FIG. 4, using nitric acid to form dinitrotoluene, wherein the dinitrotoluene has two nitro groups. The process of the present invention also comprises the step of supplying the dinitrotoluene to a toluene diamine reactor, such as reactor 308 through a line such as line 310 as shown in FIG. 4. In addition, hydrogen gas is supplied to the toluene diamine reactor through a hydrogen supply line, such as line 328 as shown in FIG. 4. In the toluene diamine reactor, the hydrogen gas reduces each of the nitro groups, respectively, to an amino group to produce toluene diamine.

In the first embodiment of the present invention, the protons in the electrochemical cell are reduced at the cathode to form hydrogen gas. The process of the present invention also includes the step of supplying the hydrogen gas formed in the electrochemical cell to the toluene diamine reactor through a hydrogen recycle line, such as line 328 as shown in FIG. 4.

In the application of the present invention as illustrated in FIG. 4, the process of the present invention also includes the step of supplying the toluene diamine to the toluene diisocyanate reactor through a line, such as line 324 as shown in FIG. 4, to produce toluene diisocyanate and molecular anhydrous hydrogen chloride. This reaction is given by equation (10) above.

Additional advantages and modifications will readily occur to those skilled in the art. The invention, in its broader aspects, is therefore not limited to the specific details and representative apparatus shown and described. Accordingly, departures may be made from such details without departing from the spirit or scope of the general inventive concept as defined by the appended claims and their equivalents.

What is claimed is:

1. A process for producing an isocyanate from chlorine gas produced by the electrochemical conversion of anhydrous hydrogen chloride to chlorine gas, comprising the steps of:

(a) supplying chlorine to a phosgene generator through a first inlet supply line and supplying carbon monoxide to the phosgene generator through a second inlet supply line, wherein the chlorine and the carbon monoxide react in the phosgene generator to produce phosgene;

(b) supplying the phosgene from the phosgene generator to an isocyanate reactor;

(c) supplying an amine to the isocyanate reactor, wherein the amine reacts with the phosgene in the isocyanate reactor to produce an isocyanate and anhydrous hydrogen chloride;

(d) supplying the anhydrous hydrogen chloride to an anode-side inlet of an electrochemical cell, wherein the electrochemical cell comprises a cation-transporting membrane, an anode disposed in contact with one side of the membrane and a cathode disposed in contact with the other side of the membrane;

(e) applying a voltage to the electrochemical cell so that the anode is at a higher potential than the cathode, and so that:
        (i) the anhydrous hydrogen chloride is oxidized at the anode to produce chlorine gas and protons,
        (ii) the chlorine gas is released from an anode-side outlet of the cell,
        (iii) the protons are transported through the membrane of the cell, and
        (iv) the transported protons are reduced at the cathode of the cell; and (f) supplying the chlorine gas released from the anode-side outlet to the phosgene generator.

2. The process of claim 1, wherein the chlorine gas released from the anode-side outlet of the cell is dry, further including the step of liquefying the dry chlorine gas in a purifier to form liquid dry chlorine.

3. The process of claim 2, further including the steps of supplying liquid dry chlorine, in addition to the liquid dry chlorine formed in the purifier, to the phosgene generator to produce phosgene.

4. The process of claim 1, wherein a portion of the anhydrous hydrogen chloride is unreacted and is released from the anode-side outlet means of the electrochemical cell, further including the step of separating the unreacted anhydrous hydrogen halide from the liquid dry chlorine.

5. The process of claim 4, further including the step of recycling the unreacted anhydrous hydrogen chloride to the anode-side inlet of the electrochemical cell.

6. The process of claim 1, wherein the isocyanate is toluene diisocyanate, further comprising the step of nitrating toluene in a dinitrotoluene reactor using nitric acid to form dinitrotoluene, wherein the dinitrotoluene has two nitro groups.

7. The process of claim 6, further comprising the steps of supplying the dinitro-toluene to a toluene diamine reactor and supplying hydrogen gas to the toluene diamine reactor, where the hydrogen gas reduces each of the nitro groups, respectively, to an amino group to produce toluene diamine.

8. The process of claim 7, wherein the protons are reduced at the cathode to form hydrogen gas.

9. The process of claim 8, further including the step of supplying the hydrogen gas to the toluene diamine reactor through a hydrogen recycle line.

10. The process of claim 7, further comprising the step of supplying the toluene diamine to a toluene diisocyanate reactor, where the phosgene and the toluene diamine react to produce toluene diisocyanate and anhydrous hydrogen chloride.

* * * * *